(12) United States Patent
Wessels et al.

(10) Patent No.: US 7,030,271 B2
(45) Date of Patent: Apr. 18, 2006

(54) MULTIFUNCTIONAL LINKER MOLECULES FOR TUNING ELECTRONIC CHARGE TRANSPORT THROUGH ORGANIC-INORGANIC COMPOSITE STRUCTURES AND USES THEREOF

(75) Inventors: Jurina Wessels, Fellbach (DE); William Ford, Stuttgart (DE); Akio Yasuda, Stuttgart (DE)

(73) Assignee: Sony International (Europe) GmbH, Berlin (DE)

( * ) Notice: Subject to any disclaimer, the term of this patent is extended or adjusted under 35 U.S.C. 154(b) by 77 days.

(21) Appl. No.: 10/006,636

(22) Filed: Dec. 6, 2001

(65) Prior Publication Data

US 2002/0127756 A1 Sep. 12, 2002

(30) Foreign Application Priority Data

Dec. 8, 2000 (EP) .................................. 00126968

(51) Int. Cl.
*C07C 233/00* (2006.01)
*C07C 333/00* (2006.01)
*C07C 333/14* (2006.01)

(52) U.S. Cl. .......................... 564/155; 564/74; 564/75; 564/123; 564/152

(58) Field of Classification Search ........ 435/DIG. 42; 568/61, 62, 67, 69; 564/155, 74, 75, 123, 564/152
See application file for complete search history.

(56) References Cited

U.S. PATENT DOCUMENTS 3,915,962 A 10/1975 Brand et al.

FOREIGN PATENT DOCUMENTS

| DE | 11 34 063 | 8/1962 |
|---|---|---|
| JP | 51042174 | * 11/1976 |
| WO | WO 96 07487 | 3/1996 |

OTHER PUBLICATIONS

R.N. Misra, et al.: "The Use of Some Thioglycollanilides in Inorganic Analysis" Journal of the Indian Chemical Society, vol. 32, 1955, pp. 127-134, XP001002394.

A.S. Aswar, et al.: "Structural and Conducting Studies on Manganese-, Cobalt-, Nickel-, Copper-, Zinc-, and Cadmium(II) Polychelates" Journal of the Indian Chemical Society, vol. 74, No. 9, Sep. 1997, pp. 679-682, XP001002395.

I.M. Sarin, et al.: "Preparation and Characterisation of Some New Polymeric Chelates of Transition Metal Ions" Asian Journal of Chemistry, vol. 10, No. 2, 1998, pp. 221-227, XP001010051.

E.B. Knott: "Heterocyclyl-Rhodamines and -2-Thiohydantoins" Journal of the Chemical Society, 1956, pp. 1644-1669, XP000943916.

E. Cullen, et al.: "BIS Basic Substituted Diaminobenzobisthiazoles as Potential Antiarthritic Agents" Journal of Medicinal Chemistry, vol. 35, No. 2, Jan. 24, 1992, pp. 350-361, XP002168973.

V.N. Elokhima, et al.: "Reaction of Acylacetylenes and Methyl Propiolate With N, N'-BIS(Dithiocarboxy) Piperazine" Bulletin of the Academy of Sciences of the USSR, Division of Chemical Science, vol. 39, No. 11, pt. 2, Nov. 1990, pp. 2390-2393, XP002168974.

(Continued)

*Primary Examiner*—Padmashri Ponnaluri
*Assistant Examiner*—Mark L. Shibuya
(74) *Attorney, Agent, or Firm*—Frommer Lawrence & Haug LLP; William S. Frommer

(57) ABSTRACT

The invention relates to tuned multifunctional linker molecules for charge transport through organic-inorganic composite structures. The problem underlying the present invention is to provide multifunctional linker molecules for tuning the conductivity in nanoparticle-linker assemblies which can be used in the formation of electronic networks and circuits and thin films of nanoparticles. The problem is solved according to the invention by providing a multi-functional linker molecule of the general structure

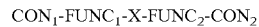

$CON_1$-$FUNC_1$-X-$FUNC_2$-$CON_2$ in which X is the central body of the molecule, $FUNC_1$ and $FUNC_2$ independently of each other are molecular groups introducing a dipole moment and/or capable of forming intermolecular and/or intramolecular hydrogen bonding networks, and $CON_1$ and $CON_2$ independently of each other are molecular groups binding to nanostructured units comprising metal and semiconductor materials.

1 Claim, 4 Drawing Sheets

OTHER PUBLICATIONS

Figure 1A:
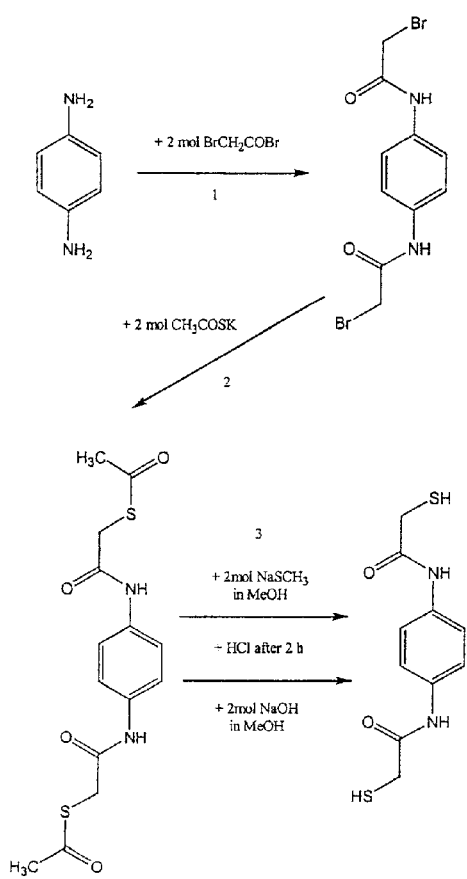

N.G. Lukyanenko, et al.: "Macroheterocycles; XX. Synthesis of Cryptands Containing Urea and Thiourea Moieties" Synthesis, No. 2, Feb. 1984, p. 137, XP002168975.

N. Uehara, et al.: "Spectrophotometric Studies for Complex Formulation of Diammonium 1, 4, 10, 13-Tetraoxa-7, 16-Diazacyclooctadecane-BIS(N-Dithioate) With Transitional Metal Ions Under Coexistence of Alkali Metal Ion and Alkaline Earth Metal Ion" Chemistry Letters, No. 7, Jul. 1999, pp. 709-710, XP002168976.

M. Brust, et al.: "Novel Gold-Dithiol Nano-Networks With Non-Metallic Electronic Properties" Advanced Materials, vol. 7, No. 9, Sep. 1995, pp. 795-797, XP000520465.

* cited by examiner

MULTIFUNCTIONAL LINKER MOLECULES FOR TUNING ELECTRONIC CHARGE TRANSPORT THROUGH ORGANIC-INORGANIC COMPOSITE STRUCTURES AND USES THEREOF

DESCRIPTION

The invention relates to tuned multifunctional linker molecules for charge transport through organic-inorganic composite structures and assemblies and devices comprising such multifunctional linker molecules. The invention further relates to the use of such tuned multifunctional linker molecules.

1-, 2-, and 3-dimensional assemblies of nanometer-sized particles coupled by multifunctional linker molecules have potential applications in nanometer-sized computational or memory devices. A key enabling technology for designing such nanoelectronic devices is the ability to tune the conductivity in such assemblies by altering the structure of the linker molecules.

The multifunctional linker molecules connect the nanoparticles with each other through tunnel barriers. It has been shown in the literature that charge transport via through-bond tunneling is a major channel for charge transport (Slowinskli, K., Chamberlain, R. V., Miller, C. J., Majda, M. (1997) J.Am. Chem. Soc., 119, 11910–11919 "Through-bond and chain-to-chain coupling. Two pathway electron tunneling through liquid alkanethiol monolayers on mercury electrodes.").

Further it has been suggested that the orbital overlap between the nanoparticle and the binding group of the linker molecule is an important factor in charge transport through these assemblies (Bakkers, E. P. A. M., Marsmann, A. W., Jenneskens, L. M., Vanmaekelbergh, D. (2000) Angewandte Chemie, 112, 2385–2388 "Abstandsabhängiger Elektronentransfer in Au/Spacer/Q-CdSe-Anordnungen."). The electrical properties of various 1-dimensional, 2-dimensional, and 3-dimensional assemblies of nanoparticles have been described in the literature. In 2-dimensional superlattice arrays of Au-nanoparticles molecularly linked by aryl di-isonitriles, both nonlinear Coulomb-charging behavior as well as Ohmic behavior has been reported in the literature (Janes, D .B., Kolaguta, V. R., Osifchin, R. G., Bielefeld, J. D., Andres, R. P., Henderson, J. I., Kubiak, C. P. (1995) Superlattices and Microstructures, 18, 275–282 "Electronic conduction through 2D arrays of nanometer diameter metal clusters.", Andres, R. P., Bielefeld, J. D., Henderson, J. I., Janes, D. B., Kolagunta, V. R., Kubiak, C. P., Mahoney, W. J., Osifchin, R. G. (1996) Science, 273, 1690–1693, "Self-assembly of a two-dimensional superlattice of molecularly linked metal clusters.", Chen, E., Ahmed, H., Nakazoto, K. (1995) Applied Physics Letters. 66, 3383–3384 "Coulomb blockade at 77K in nanoscale metallic islands in a lateral nanostructure."). Ohmic charge transport has been observed in 3-dimensional arrays of Au and Ag nanoparticles. The resistance in such films can vary between $R>10^7$ $\Omega$ to $R<10^2$ $\Omega$, analogous to what has been observed in percolated films of metal grains depending on the grain size and the dot to dot distances (Musick, M. D., Keating, C. D., Keefe, N. H., Natan, M. J . (1997) Chem. Mater., 9, 1499–1501 "Stepwise construction of conductive Au colloid multilayers from solution.", Neugebauer, C. A., Webb, M. B. (1962) Journal of Applied Physics, 33, 74–82 "Electrical conduction mechanism in ultrathin, evaporated metal films.").

WO 96/07487 describes the synthesis of nanoparticle materials exhibiting controlled electronic, magnetic and/or optical properties. Such synthesized materials can then be incorporated into electronic, magnetic and/or optical devices, such as, for example, resistors, diodes, transistors, switches, displays, lasers, photovoltaic and magnetic devices. Further, the application describes the production of thin film structures that can be used for said devices.

In addition, a 1-step formation of 3-dimensional nanoparticles is described via the preparation of a co-solution of nanoparticles and linker molecules and exposing this to a functionalized substrate. WO 96/07487 also describes a layer-by-layer assembly technique for producing thin film structures from particles of nanometer dimensions and polyfunctional linker molecules comprising a hydrocarbon skeleton with at least two functional groups (which may be the same or different) capable of binding to other particles or substrates.

W096/07487 further proposes a prototype of a nanostructured array of quantum dots with adjustable electronic conductivity in the range typical for semi-conductors. The properties of the material can be tuned by building moieties into the linker molecules that can act as electron donors or acceptors. Further, the resistivity of the material changes dramatically as a function of the chain length of the linker molecule.

W096/07487 in general suggests activated electron hopping as the principle mechanism for charge transport.

Nevertheless, despite the above-mentioned progress, there is still the need in the art to improve multifunctional linker molecules in order to allow the tuning and/or fine tuning of the conductivity of nanostructure assemblies from the insulating to the conducting limit.

Accordingly, the problem underlying the present invention is to provide improved multifunctional linker molecules for tuning the conductivity in nanoparticle-linker assemblies which may be used, e.g., in the formation of electronic networks and circuits and thin films of nanoparticles allowing a high density arrangement.

The problem is solved according to the invention by providing a multifunctional linker molecule of the general structure

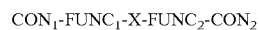

$CON_1$-$FUNC_1$-X-$FUNC_2$-$CON_2$ in which

X is the central body of the molecule, $FUNC_1$ and $FUNC_2$ independently of each other are molecular groups introducing a dipole moment and/or capable of forming intermolecular and/or intramolecular hydrogen bonding networks, with the provisio that they are not of hydrocarbon nature, and $CON_1$ and $CON_2$ independently of each other are molecular groups binding to nanostructured units comprising metal, alloys of metals, metal core/shell materials, semiconductor or semi-conductor core shell materials.

The multifunctional linker molecule according to the invention has several advantages over the linker molecules described in WO 96/07487. First, the general structures are different in that the general structure of the linker of WO 96/07487 can schematically be seen as [Connecting group] [Hydrocarbon skeleton] [Connecting group] in which the connecting group is capable of binding to nanoparticles.

In contrast, the general structure of the multifunctional linker molecule according to the invention can be represented as [Connecting group 1][Functional group 1][Central body][ Functional group 2] [Connecting group 2] in which functional groups are introduced between the central body and the connecting groups which are capable of binding to nanoparticles. The functional groups introduce different specific functions into the inventive linker molecule and are not of hydrocarbon nature. Therefore, the molecular structure of the multifunctional linker molecule is different from WO 96/07487, which results in a drastic improvement of the cpability for tuning the charge transport through organic/inoganic composite structures according to the invention.

The functional groups add the aspects of introducing a dipole moment into the structure and forming intermolecular and/or intramolecular hydrogen bonding networks. These features can support the ordering of the organic/inorganic composite structures and allows the tuning of the charge transport.

Thus, the design of the linker molecules according to the invention provides a means of tuning the conductivity through these assemblies. To the inventors knowledge, so far a concept of how to alter molecular properties in order to tune the charge transport has not been suggested. This invention concerns a strategy for tuning the conductivity through such assemblies by altering specific parts of multifunctional linker molecules providing a molecular tool-box that allows tuning of the conductivity in such assemblies from the insulating to the conducting limit. This is again in contrast to WO 96/07487, which allows tuning of the conductivity only in the semiconducting range.

Preferred is a multifunctional linker molecule according to the invention, in which CON and $CON_2$ are identical or different and $FUNC_1$ and $FUNC_2$ are identical or different.

In one embodiment, the multifunctional linker molecule according to the invention is characterized in that it exhibits a length between about 8 Å and about 30 Å.

Preferred is a multifunctional linker molecule according to the invention in which X is a structure having a hydrocarbon skeleton with two identical or different substitutes that are used for connecting to and/or forming of the molecular groups $FUNC_1$ and $FUNC_2$.

The central part of the linker molecule can also consist of alkanes, alkenes, alkynes, and combinations thereof which exhibit two end groups comprising amines, carboxylic acids, sulfonic acids and phosphoric acids.

Further preferred is a multifunctional linker molecule according to the invention, which is characterized in that the substitutes of X are selected from the group comprising amines, carboxylic acids, sulfonic acids and phosphoric acids. Even more preferred is, that the substitutes of X are directed at an angle α relative to one another such that $90° < α < 270°$.

In yet another embodiment of a multifunctional linker molecule according to the invention, X comprises a conjugated system, an aromatic π-system and/or contains heteroatoms, like N, O or S, and/or contains at least one electron donating substituent, like $CH_3$, $O^-$, $COO^-N(CH_3)_2$ or $NH_2$ and/or electron accepting substituent, like CN, $COCH_3$, $CONH_2$, $CO_2CH_3$ $N(CH_3)_3^+$, $NO_2$, F, Cl, Br, I, $OCF_3$, or $SO_2NH_2$. two end substitutes as mentioned above;

b) structures having the general formula

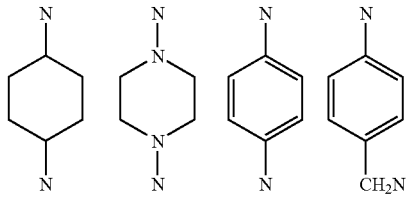

-continued

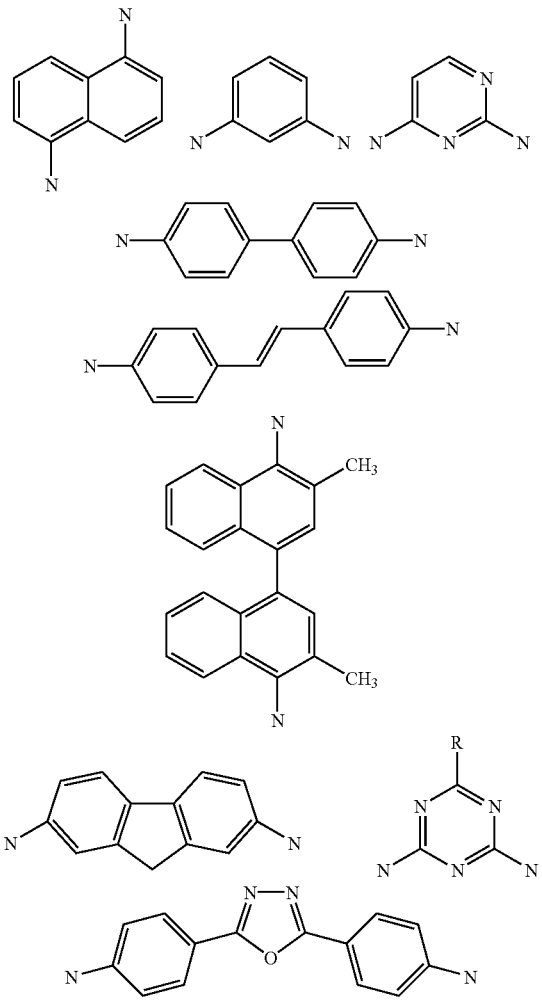

and derivatives thereof containing heteroatoms, like N, S, and/or O, or electron donating or accepting substitutes; R can be methyl, phenyl or alkoxyl and wherein $FUNC_1$ and $FUNC_2$ are attached via the N-atoms of the two amine substitutes indicated by N; structures having the general formula

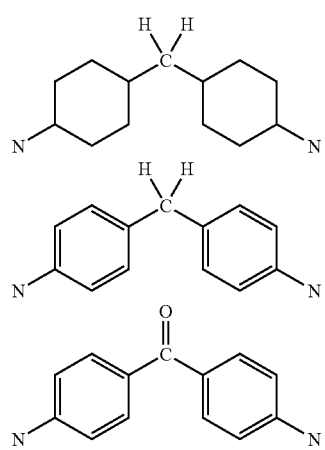

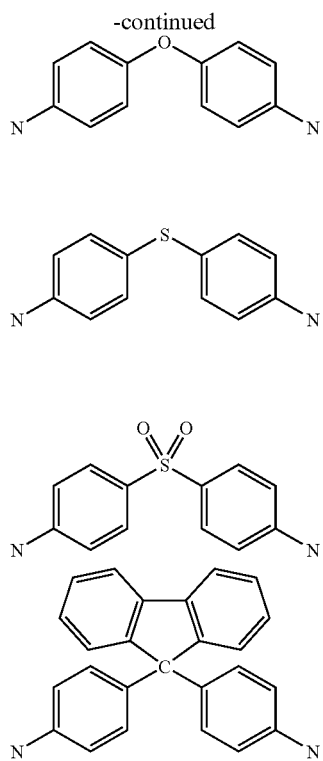

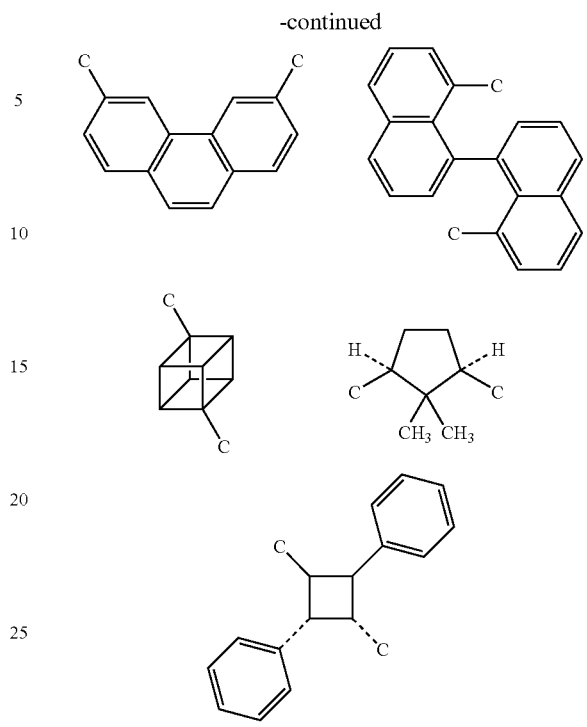

and derivatives thereof containing electron donating or accepting substitutes wherein FUNC$_1$ and FUNC$_2$ are attached via the N-atoms of the amine indicated by N; structures having the general formula and derivatives thereof containing heteroatoms, like N, S, and/or O, or electron donating or accepting substitutes; and wherein FUNC$_1$ and FUNC$_2$ are attached via the carbon atoms of the two carboxylic acid substitutes indicated by C; structures having the general formula

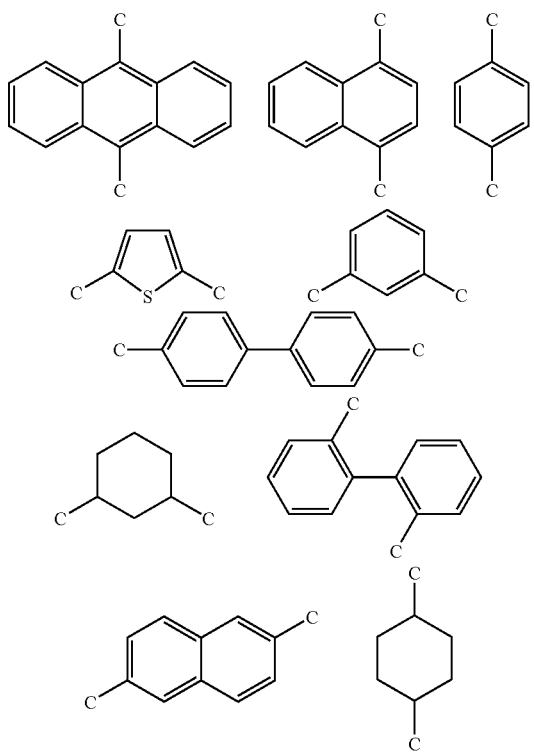

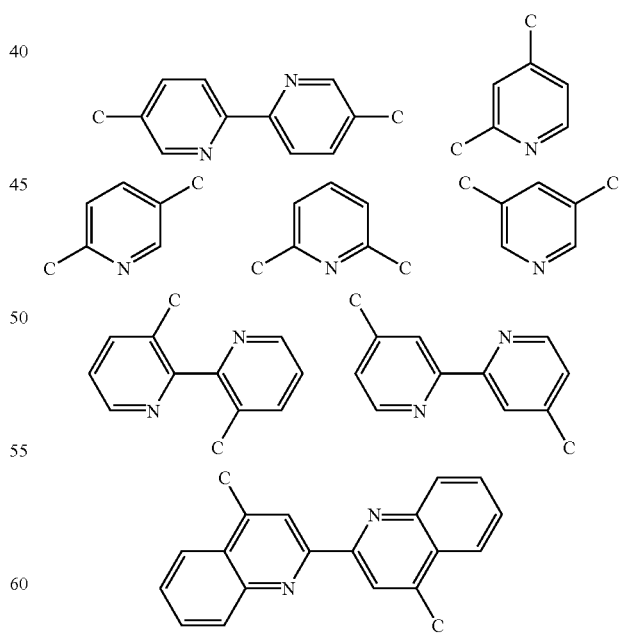

wherein FUNC$_1$ and FUNC$_2$ are attached via the carbon atoms of the two carboxylic acid substitutes indicated by C; structures having the general formula

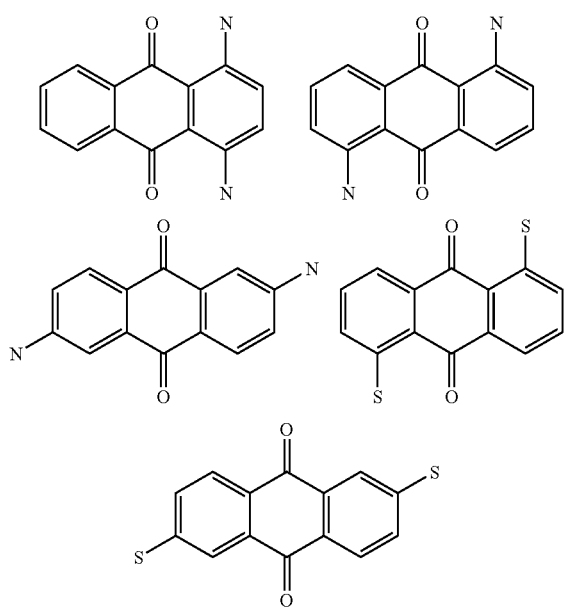

and derivatives therefore containing electron donating or accepting substitutes wherein $FUNC_1$ and $FUNC_2$ are attached via the N- or S-atoms of the two amine or sulfonic acid substitutes indicated by N and S; structures having the general formula

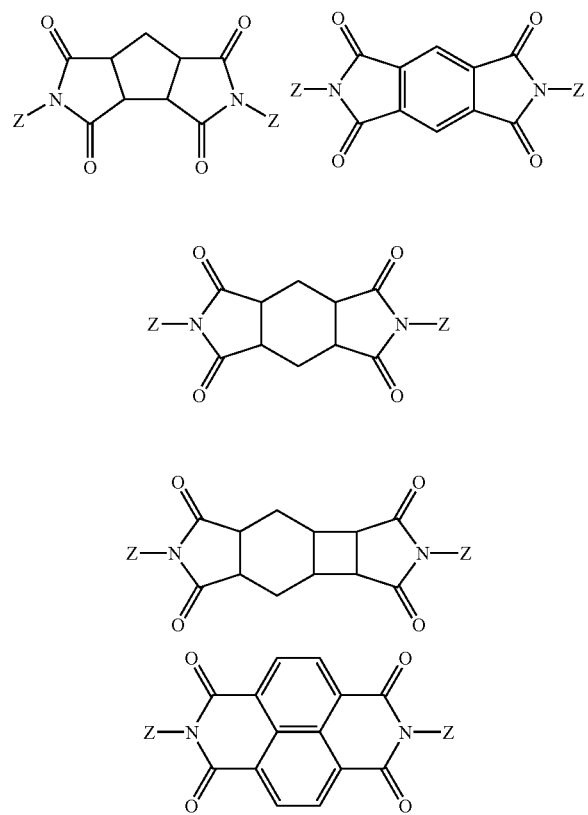

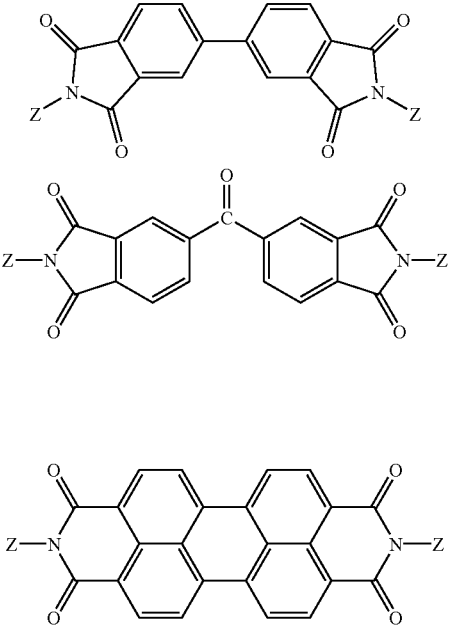

in which Z represents amine (Z=N) or a carboxymethyl (Z=CH(R)C) residue, wherein R is an amino acid side chain and $FUNC_1$ and $FUNC_2$ are attached via Z; and c) electron donors like hydroquinones and electron acceptors, like quinones and diimides carrying two substitutes as mentioned above.

In a still further embodiment according to the invention, the multifunctional linker molecule is characterized in that $FUNC_1$ and $FUNC_2$ independently of each other are connected to X via N, C, S, or P, and are selected from the group including —NH—NHCO, —NHCONH, —NHCSNH,—NHCONHNH, —NHCSNHNH, —NHCONHNHCO, and —NHCONHNHCOin case of a connection via N; —CONH, —CONHNH, and —CONHNHCOin case of a connection via C; —SO$_2$NH, —SO$_2$NHNH, and —SO$_2$NHNHCOin case of a connection via S; and —PO$_2$NH, —PO$_2$NHNH, and —PO$_2$NHNHCOin case of a connection via P.

In an even more preferred embodiment of a multifunctional linker molecule according to the invention, $CON_1$ and $CON_2$, connected to FUNCand $FUNC_2$ via NHor CO, independently of each other are selected from the groups including —(CHR)$_n$COOH; —(CHR)$_n$NC; —(CHR)$_n$NH$_2$; —(CHR)$_n$NHCS$_2$H; —(CHR)$_n$OPO$_3$H$_2$; —(CHR)$_n$OSO$_3$H; —(CHR)$_n$PO$_3$H$_2$; —(CHR)$_n$SH; —(CHR)$_n$SO$_3$H; —CSOH; and —CS$_2$H in case of a connection via NH; and —(CHR)$_n$COOH; —(CHR)$_n$NC; —(CHR)$_n$NH$_2$; —(CHR)$_n$NHCS$_2$H; —(CHR)$_n$OPO$_3$H$_2$; —(CHR)$_n$OSO$_3$H; —(CHR)$_n$ PO$_3$H$_2$; —(CHR)$_n$SH; and —(CHR)$_n$SO$_3$H in case of a connection via CO;

where R is H, CH$_2$OH, or CH$_3$ and n is 1 or 2, and ionic forms thereof.

One example of how the different units can be put together can schematically be described as follows:

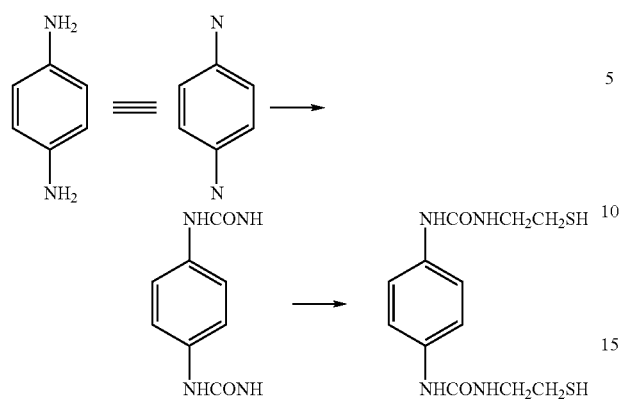

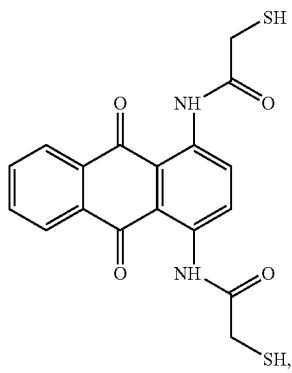

1,4-dimercaptoacetamido-9,10-anthraquinone, having the formula

In a further embodiment of the inventive multifunctional linker molecule, the thiocarbamates formed from secondary amines are directly attached to the central body X.

Other preferred embodiments of the inventive multifunctional linker molecule are characterized in that $CON_1$ and $CON_2$ independently of each other comprise branched molecular structures.

Most preferred is a multifunctional linker molecule which is selected from the group including 1,4-dimercaptoacetamidobenzene derivatives of the general formula

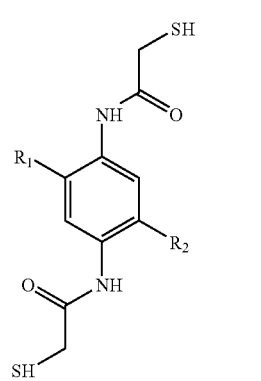

1,5-dimercaptoacetamido-9,10-anthraquinone, having the formula

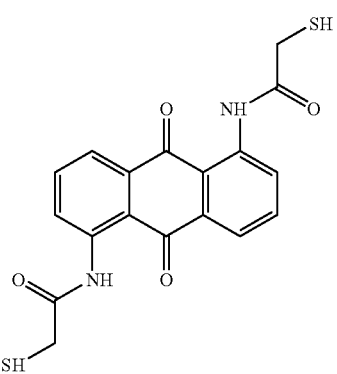

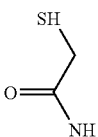

in which $R_{1,2}$ is independently selected from $CH_3$ and/or Cl, 1,4-dimercaptoacetamidocyclohexane having the formula

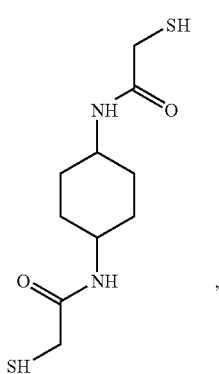

1,8-dithiocarbamatobenzene, having the formula

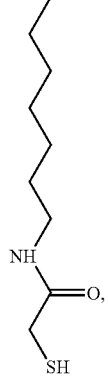

1,4-dithiocarbamatobenzene, having the formula

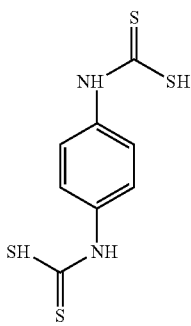

and 1,4-dithiocarbamatocyclohexane, having the following formula

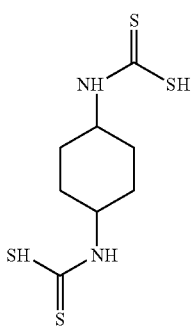

Other preferred embodiments of the multifunctional linker molecule according to the invention are selected from the group of the following formulae:

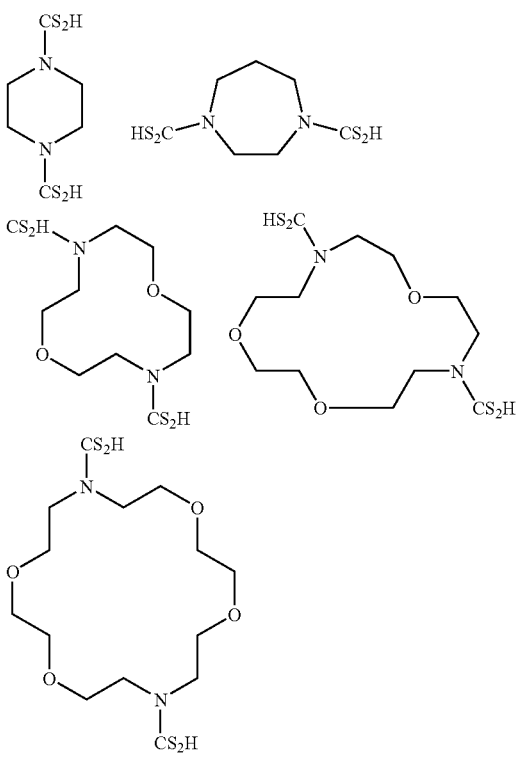

In an even more preferred embodiment of the invention, the multifunctional linker molecule is characterised in that the electron density on aromatic π-systems—as it can be described through the Harnmett correlation parameter—and/or the degree of conjugation of the linker molecule is altered.

Another aspect of the invention is a 1-, 2-, or 3-dimensional assembly of nanostructured units comprising a multifunctional linker according to the invention wherein the conductivity of the assembly is determined by the structure of the multifunctional linker molecule.

Preferably, the assembly according to the invention is characterised in that the nanostructured units are selected from the group comprising nanoparticles, such as metal, semiconductor, or core/shell semiconductor nanoparticles, nanowires, nanotubes, nanobelts, and electrodes.

The problem of the invention is further solved by an assembly, which is characterised in that the absorption of the plasmon band is located between 500 nm and 600 nm, the functional units are Au-nanoparticles, the size of said Au-nanoparticles is about 5 to about 20 nm, the resistivity of the assembly is of the order of $10^2$ Ω cm for a film thickness of about 30 nm, and the resistivity increases with decreasing temperature.

More preferred is an assembly which is characterised in that the absorption maximum of the plasmon band is located between 600 nm and 700 nm, the functional units are Au-nanoparticles, the size of said Au-nanoparticles is about 5 to about 20 nm, the resistivity of the assembly is of the order of $10^{-1}$ to 10 Ω cm for a film thickness of about 30 nm, and the resistivity increases with decreasing temperature.

Most preferred is an assembly according to the invention which is characterised in that the absorption spectrum shows the absorption characteristics of bulk metal films, the functional units are Au-nanoparticles, the size of said Au-nanoparticles is about 5 to about 20 nm, the resistivity of the assembly is of the order of $10^{-2}$ Ω cm for a film thickness of about 30 nm, and the resistivity decreases with decreasing temperature.

In a still further aspect of the invention, the problem is solved by the use of an assembly according to the invention as interconnects between nanowires and nanostructured units in 1-, 2-and 3-terminal devices, self-assembled metal coatings and/or self-assembled electrodes.

The inventors of the present application have surprisingly found that a new design of nanoparticle linker molecules allows the effective tuning of the charge transport in nanoparticle linker assemblies from the insulating to the conducting limit.

The inventors of the present invention have provided a method for tuning the charge transport through such assemblies by altering specific parts of the multifunctional linker molecules which provides a molecular tool-box that allows tuning of the charge transport in such assemblies from the insulating to the conducting limit. To the inventor's knowledge, so far a concept of how to alter molecular properties in order to tune the charge transport has not been suggested.

Tuning of the charge transport is in one embodiment achieved by altering the energy levels of the molecular orbitals and the bonds formed between the nanoparticle and linker molecule. Four different means for altering the multifunctional linker molecules for tuning the charge transport through these assemblies are considered in this invention:

1) Altering of the electron density on aromatic π-systems through different substitutes as it can be described through the Hammett correlation parameter $\sigma_p^+$.

It is important for the design of nanostructured electronic devices to have means for fine tuning the HOMO-LUMO levels of the linker molecules, in order to adjust the HOMO and LUMO levels of the linker molecules with respect to the Fermi energy level of metal particles as well as the energy band levels of semiconducting particles. In this invention, we provide a new approach for providing a series of linker molecules exhibiting an aromatic π-system where the electron density on the aromatic π-system of the multifunctional linker molecule is varied in a defined manner as it can be described by the so-called Hammett correlation parameter $\sigma_p^+$. This parameter describes the electron donating and accepting properties of substitutes on aromatic π-systems, which alter the energy gap between the HOMO and LUMO energy levels in the linker molecules, and hence provides a means for fine-tuning the charge conduction through the assemblies.

2) Altering the degree of charge transport through linker molecules exhibiting conjugated π-systems;

a) Altering the particle-particle interaction by changing the degree of conjugation in the linker molecule through cross-conjugation an/or by introducing non-conjugated molecular structures into the linker molecule.

b) Introducing electron-accepting groups onto conjugated π-systems of the linker molecule, facilitating the electron transport across the linker molecule.

The possibilities for influencing charge transport by changing the degree of delocalisation in conjugated π-systems via cross-conjugation has been suggested for molecular wires. Theoretical calculations have shown that in case of molecular wires made out of coupled porphyrin systems, cross conjugation leads to a pronounced attenuation of the coupling interaction between HOMO-orbitals (Hush, N. S., Reimers, J. R., Hall, L. E., Johnston, L. A., Crossley, M. J. (1998) Annals of the New York Academy of Sciences, 852, 1–21 (Edts. Aviram, A., Ratner, M.) "Optimization and chemical control of porphyrin-based molecular wires and switches."). Cross-conjugation interrupts the long-range electronic coupling of conjugated π-bonds and hence it is a possibility to fine-tune the conductivity of linker molecules exhibiting conjugated π-systems.

Besides the possibility of influencing the charge transport in conjugated linker molecules via cross-conjugation the charge transport can also be altered by introducing electron accepting groups into the linker molecules. Quinones are very efficient electron acceptors that are implemented into the light harvesting systems of plants. It has been suggested that they have been developed by the plants in order to facilitate electron transport in the photosynthetic system. Similarly it can be envisioned that efficient electron acceptors such as anthraquinones (Karuktis, K. K., Gruber, S. M., Fruetel, J. A., Boegeman, S. C. (1988) Biochim. Biophys. Acta, 932, 84–90 "Quenching of chlorophyll fluorescence by substituted anthraquinones.") for example can facilitate the electron transport in such multidimensional assemblies.

3) Influencing the charge transport properties through the contacting molecular groups $CON_{1,2}$.

The molecular groups forming the connection between the different nanostructured units, e.g. wires, active elements, and possibly electrodes have a central function in the charge transport, since the molecular design of this group is defining the type of bond that is formed the linker molecule and the different nanostructured units. Included is also, that the electrode or wire metal can be altered to alter the atom from the nanostructured unit that participates in forming the contact to the linker molecule depending on what type of tunnel barrier should be established for a specific interconnect.

The role of the contacts has been studied theoretically by implementing the contacts to Au-particles into the extended calculations of the HOMO and LUMO levels of a 1,4 benzene dithiolate (Emberly, E. G., Kirczenow, G. (1998) Annals of the New York Academy of Sciences, 852, 1–21 (Edts. Aviram, A., Ratner, M.) "Theory of electrical conductance through a molecule."). These calculations show that, in a model system consisting of two Au-particles connected by one benzene dithiolate, conduction can occur via two pathways:

a) Through the states derived from the benzene dithiolate HOMO and LUMO levels.

b) Through the energy levels arising from hybrid Au particle-benzene dithiolate states.

However, the linker molecule/particle interface has a very low density of states. Experiments by Reed et al. suggest that the contacts are atomically terminated, i.e. the S-atoms are attached to single Au-atoms (Reed, M. A., Zhou, C., Mueller, C. J., Burgin, T. P., Tour, J. M. (1997) Science, 278, 252). It has been shown for Au-S systems, that the Au atom cocontributes states at the Fermi level, while the S atom contributes p states, thereby forming a bonds (Di Ventra, Pantelidis, S. T., Lang, B. D. (2000) Phys. Rev. Lett., 84, 979–982 "First—principles calculation of transport properties of a molecular wire.", Johansson, A., Stafström, S. (2000) Chem. Phys. Lett., 322, 301–306 "Interactions between molecular wires and a gold surface."). Thus the linker molecule/particle interface forms a tunnel barrier for the charge transport. Therefore, binding of the linker molecule via single or multiple binding groups, e.g. thiols or thiocarbamates, should have a strong influence on the properties of the tunnel barrier and hence on the charge transport through these assemblies.

Further, theoretical calculations have shown that replacement of Au atoms by Al atoms should reduce the tunnel barrier. Al atoms can contribute to the interconnect p-orbitals and thus are capable to form π-orbitals with S atoms of linker molecules (Di Ventra, Pantelidis, S. T., Lang, B. D. (2000) Phys. Rev. Lett., 84, 979–982 "First—principles calculation of transport properties of a molecular wire.").

4) Influencing the charge transport by altering the functional groups of the linker molecule that is located at the nanoparticle/linker molecule interface: Increasing the electron coupling through two interconnected circuit elements by introducing a hydrogen-bonding network into the linker molecules.

It has been shown that a hydrogen bond network linking amide bonds in alkane monolayers leads to an increase in the electronic coupling between an electrode and a ferrocene molecule (Sek, S., Misicha, A., Bileicz, R. (2000) J. Phys. Chem. B, 104, 5399–5402 "Effect of inter-chain hydrogen bonding on electron transfer through alkanethiol monolayers containing amide bonds."). The same effect has also been observed for the electron tunneling between mercury-mercury tunnel junctions across alkane-thiolate bilayers (Slowinski, K. Fong, H. K., Mayda, M. (1999) J. Am. Chem. Soc., 121, 7257–7261 "Mercury-Mercury tunneling junctions. 1. Electron transfer across symmetric and asymmetric alkane thiolate bilayers.").

It is to be understood that the term "nanoparticle" according to the scope of the invention is used generically. It includes all varieties of metal and semiconducting nanoparticles and "clusters". The sizes of the nanoparticles can vary between 0.8 nm and up to the order of a few 100 nm. Further, on the interconnecting, linker molecules can establish interconnects between at least two nanoparticles, between at least one nanoparticle and a nanowire, between at least two nanowires, nanotubes or nanobelts, as well as between at least one nanoparticle or one nanowire, nanotube or nanobelt and macroscopic electrodes. Thus, "assemblies" refers to one-, two-, and three-dimensional assemblies of the above mentioned systems in all possible combinations.

Various types of metal or semi-conducting nanoparticles can be interconnected into one-, two-, or 3-dimensional arrays of nanoparticles. The synthesis of various nanoparticles is described in the literature as well as in patents. Depending on the preparation method and the capping molecule used, the nanoparticles can be prepared exhibiting different sizes. The preparation methods as well as the capping molecule largely determine the size distribution of the nanoparticles. A requirement for the successful assembly of the nanoparticles into an array is that the linker molecule can readily displace the capping molecule. In case a particular capping molecule can not be displaced by the linker molecules, the capping molecule could be exchanged with a different kind of capping molecule in a ligand exchange reaction prior to the assembly process (Jahn, W. (1999) Journal of Structural Biology, 127, 106–112 "Review: Chemical aspects of the use of gold clusters in structural biology.", Brown, L. O., Hutchinson, J. E. (1997) J. Am. Chem. Soc., 119, 12834–12835 "Convenient preparation of stable, narrow-dispersity, gold nanocrystals by ligand exchange reactions.", Aguila, A. Murray, R. W. (2000), Langmuir, 16, 5949–5954 "Monolayer-protected clusters with fluorescent dansyl ligands.").

The synthesis of the multifunctional, i.e. bi-, and polyfunctional linker molecules is based on substitution reactions that are described in the literature. Two possible synthetic routes are considered. In route 1, the amino substitutes of the starting materials are converted into bromoacetamido groups via a nucleophilic substitution reaction with bromoacetylbromide. In the second step, the bromoacetamido group is converted into a thioacetate ester by reaction with potassium thioacetate. The thioacetate ester is converted into a thiol via a cleavage reaction as it is described by Yelm (Yelm, K. E. (1999), Tetrahedron Letters 40, 1101–1102. "A simple method for in situ generation of thiols from thioacetates.") as well as Wallace and Springer (Wallace, O. B., Springer, D. M. (1998) Tetrahedron Letters, 39, 2963–2964. "Mild, selective deprotection of thioacetates using sodium thiomethoxide."). Alternatively, the reaction can be carried out as described by Martin (Martin, T. A.; Comer, W. T.; J. Med. Chem. (1985), 28, 910–914 "N-[[(Mercaptoacetyl)amino]benzoyl]glycines as mucolytic agents") in an aqueous methanolic NaOH solution. A one step reaction pathway for preparing different chelates from bis(mercaptoacetamide)-p-phenylenediamine has been described by Aswar, A. S. and Bhadange, S. G. (J. Indian Chem. Soc. (1997) 74, 679–682). The reaction is shown in FIG. 1a (prior art). In route 2, the amino substitutes are directly reacted with carbon disulfide and base to give thiocarbamate salts. This reaction is described in references (McCubbin, Q. J., Stoddart, F. J., Welton, T., White, A. J. P L., Williams, D. J. (1998), Innorganic Chemistry 37, 3753–3758. "Dithiocarbamate-functionalised dendrimers as ligands for metal complexes.", Almirall, E ., Fragoso, A., Cao, R. (1999) Electrochemistry Communications 1, 10–13. "Molecular recognition of a self-assembled monolayer of a polydithiocarbamate dervative of β-cyclodextrin on silver.", Matsumoto, I., Nakagawa, K., Matsuzaki, M., Horiuchi, K. (1975), U.S. Pat. No. 3,875,170 "Pyridine-bis-(dithio)-carbamate derivatives.") and depicted in FIG. 1b (prior art).

Different means for the assembly of the thin films have been described in the literature and in patents. The first layer of nanoparticles can be deposited onto a substrate by means of self-assembling bi-functional organic monolayers as bridge compounds. The first layer of nanoparticles can self-assemble on the functional substrate and be subsequently interconnected by the linker molecules. The linker molecules displace the capping molecules from the surface of the nanoparticles leaving a free linker group, e.g. a thiol group at the top of the nanoparticle film for the assembly of the next nanoparticle layer. This assembly process is also referred to as the layer-by-layer assembly technique (Brust, M., Bethell, D., Kiely, C. J., Schiffrin, D. J., (1998) Langmuir, 14, 5425–5429 "Self-assembled gold nanoparticle thin films with nonmetallic optical and electronic properties."). Alternatively, a one-step formation of 3-dimensional nanoparticles can be achieved via the preparation of a co-solution of nanoparticles and linker molecules and exposing this to a functionalised substrate (Whetten, R. L., Khoury, J. T., Alvarez, M. M., Murthy, S., Vezmar, I., Wang, Z. L., Stephens, P. W., Cleveland, C. C., Luedtke, W. D., Landmann, U. (1996) Adv. Mater., 8, 428). A close packed monolayer of nanoparticles can also be produced using the Langmuir-Blodgett or the Langmuir-Schaeffer technique (Musick, M. D., Keating, C. D., Keefe, N. H., Natan, M. J. (1997) Chem. Mater., 9, 1499–1501 "Stepwise construction of conductive Au colloid multilayers from solution.", Markkovich; G., Leff, D. V., Chung, S. Q., Soyez, H. M. Dunn, B., Heath, J. R. (1997) Applied Physics Letters, 70, 3107–3109 "Parallel fabrication and single-electron charging of devices based on ordered, two-dimensional phases of organically functionalized metal nanocrystals.") These techniques allow the transfer of a well-defined monolayer to a substrate, the packing density of which can be determined through the compression of the nanoparticle film at the air-water interface. Instead of using multifunctional organic molecules as bridge compounds it is also possible to deposit e.g. charged nanoparticles onto a substrate utilizing electrostatic interactions (Sato, T., Haskko, D., Ahmed, H., (1996) EP0788149A1 "Method of depositing nanometre scale particle.", Ahmed, H., Sato, T. (1998) EP0865078 "Method for depositing nanometer scale particles.").

For certain metal particles, the assembly process can be monitored using absorption spectros-copy. The optical density of the plasmon band provides information about the thickness of the self-assembled film. Furthermore, depending on the material and composition of the nanoparticles the absorption spectrum contains also information about the character of the nanoparticle film, since the optical properties of the particles are determined by the contributions from the individual particles and the collective properties of the ensemble. The plasmon band is attributed to the collective oscillations of the free conduction electrons and their response to an incident electromagnetic field. It can be considered as a hybrid resonance from the co-operative behaviour of the d-band and conduction electrons. A simple description of the plasmon frequency combining the resonance condition and the dielectric constant for a free electron gas is:

$$\varpi_{max} = \frac{ne^2}{\varepsilon_0 m_{eff}\sqrt{1+\varepsilon_m}}$$

where n denotes the electron density and $m_{eff}$ the effective mass of the electron. It has been shown in the literature, that the material dielectric function which includes core polarisation effects and the full Mie expression have to be used to describe the surface plasmon absorption correctly (Link, S., Wang, Z. L., El-Sayed, M. A. (1999) J. Phys. Chem., 103, 3529–3533 "Alloy formation of gold-silver nanoparticles and the dependence of the plasmon absorption on their composition.", Alvarez, M. M., Khoury, J. T., Schaaff, T. G., Shafigulli, M. N., Vezmar, I., Whetten, R. L. (1997) J . Phys. Chem., 101, 3706–3712 "Optical absorption spectra of nano-crystal gold molecules."). Included into the description of the plasmon frequency is the dependence on the electron density and on the effective mass or optical mass of the electron, which includes the coupling of the free electrons to the ion core (Kreibig, U., Genzel, L. (1985) Surface Science, 156, 678–700 "Optical absorption of small metallic particles."). Thus it is possible to gain some information about the electronic interaction of particles in the assembly from the absorption spectrum.

For semiconducting nanoparticles, the band-gap absorption can be used for monitoring the assembly process.

The electrical properties of such one-, two-, or, three-dimensional arrays of nanoparticles are determined by material composition and size of the nanoparticles used, the stabilising organic ligand, and by the properties of the linker molecules. Arranging small particles into an array exhibiting small spatial distance, tunnel junctions exhibiting an electrical capacitance of less than $10^{-18}$ F are created (Single charge tunnelling—Coulomb blockade phenomena in sol-ids; Eds. Devoret, M. H., Grabert, H. (1992) Nato ASI Series, Vol. 294, Plenum, N.Y.). The insulating molecular layer around the nanoparticle that serves as an insulating barrier facilitates electron tunnelling or hopping. The charge transport in these structures can be tuned from the metallic to the insulating limit by varying the size of the particles and the strength of the coupling between them.

The electron transport properties of these thin films depend on the properties of the insulating layer and the linker molecules (Brust, M., Bethell, D., Kiely, C. J., Schiffrin, D. J., (1998) Langmuir, 14, 5425–5429 "Self-assembled gold nanoparticle thin films with nonmetallic optical and electronic properties.", Neugebauer, C. A., Webb, M. B. (1962) Journal of Applied Physics, 33, 74–82 "Electrical conduction mechanism in ultrathin, evaporated metal films."). Activation energies in the range between 30–100 meV depending on the electronic structure of the linker molecule, the dot to dot distance and the size of the nanoparticles, have been reported for such assemblies (Brust, M ., Bethell, D., Schiffrin, D. J., Kiely, C. J. (1995) Advanced Materials, 7, 795–797. "Novel gold-ditiol nano-networks with non-metallic electronic properties.", Janes, D, Kolaguta, LV. R., Osifchin, R. G., Bielefeld, J. D., Andres, R. P., Henderson, J. I., Kubiak, C. P. (1995) Superlattices and Microstructures, 18, 275–282 "Electronic conduction through 2D arrays of nanometer diameter metal clusters." , Brust, M., Bethell, D., Kiely, C. J., Schiffrin, D. J., (1998) Langmuir, 14, 5425–5429 "Self-assembled gold nanoparticle thin films with nonmetallic optical and electronic properties.").

The invention is now further illustrated by the accompanying figures and examples from which further embodiments, features and examples may be taken.

FIG. 1: Schematic drawing of the synthetic routes for substituting amino functionalised molecules with dimercaptoacetamido groups (a) or with thiocarbamates (b).

Figure 2:
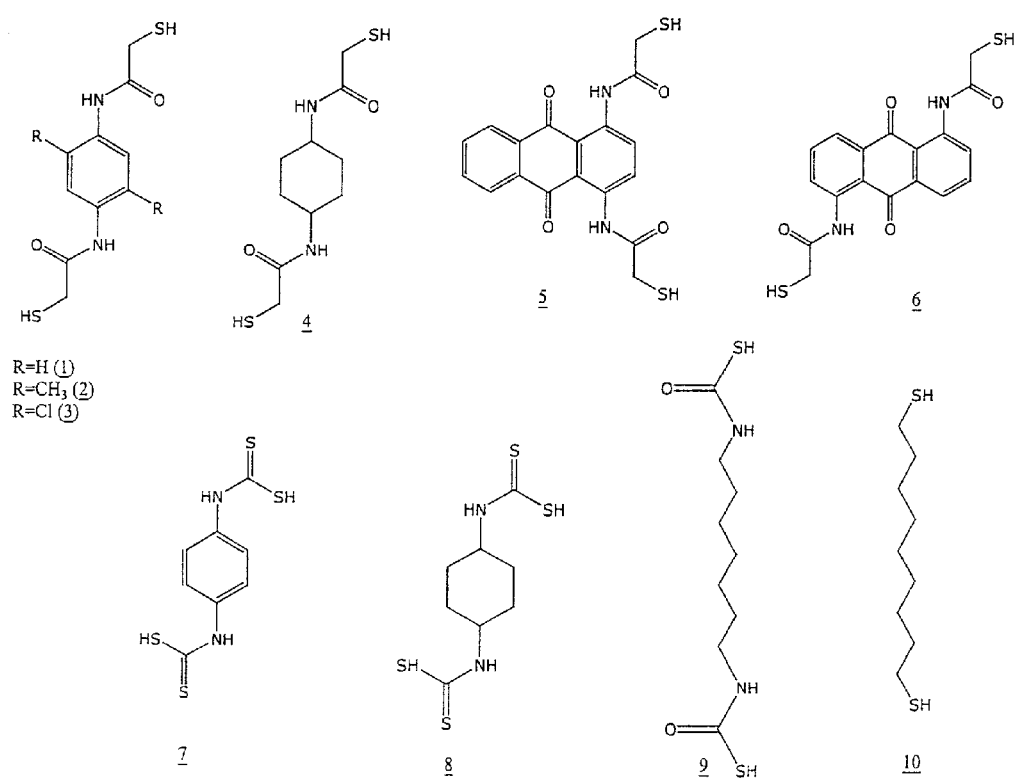

FIG. 2: Schematic drawing of the linker molecules synthesised according to the routes described in FIG. 1a and b. 1,4-dimercaptoacetamidobenzene (1), 1,4-dimercaptoacetamido-2,5-dimethylbenzene (2), 1,4-dimercaptoacetamido-2,5-dichlorobenzene (3), 1,4-dimercaptoacetamidocyclohexane (4), 1,4-dimercaptoacetamido-9,10-anthraquinone (5), 1,8-dimercaptoacetamido-9, 10-anthraquinone (6), 1,4-dithiocarbamatobenzene (7), 1,4-dithiocarbamatocyclohexane (8), 1,8-dimercaptoacetamidoctane (9), and the commercially available nonanedithiol (10).

Figure 3:
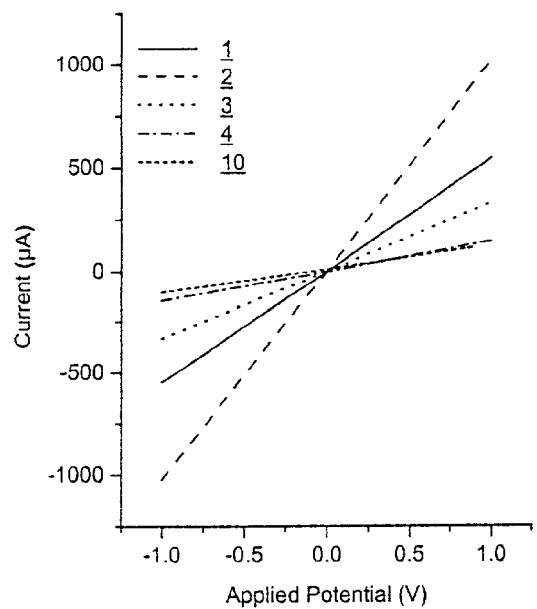

FIG. 3: I–V characteristics of Au-nanoparticles interconnected by the linker molecules 1 (-), 2 (- - -), 3 (....),4 (.-.-.), and 10 (- - -) and self-assembled onto interdigiated Au electrode structures by the layer-by-layer assembly technique to a film thickness of approx. 30 nm.

Figure 4:
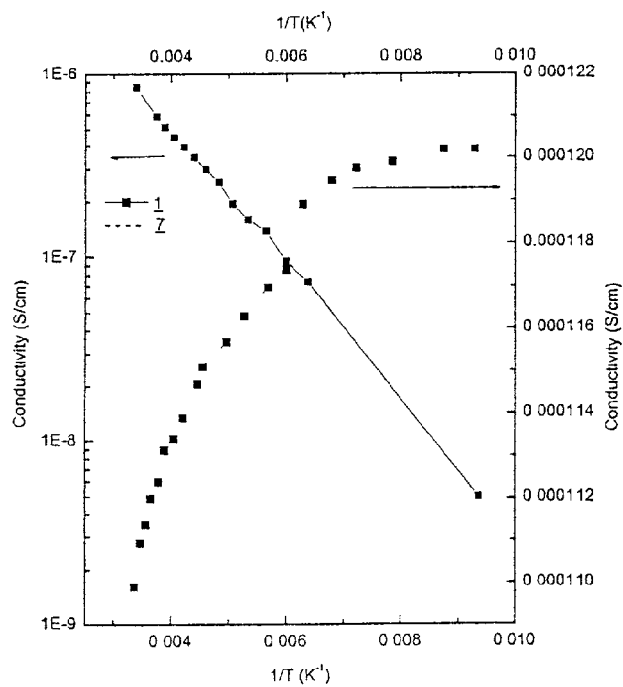

FIG. 4: Temperature dependence of the conductivity of Au-nanoparticles interconnected by the linker molecules 1 (-) and 7 (- - -) and self assembled onto interdigitated Au-electrode structures by the layer-by-layer assembly technique to a film thickness of approx. 30 nm.

Figure 5:
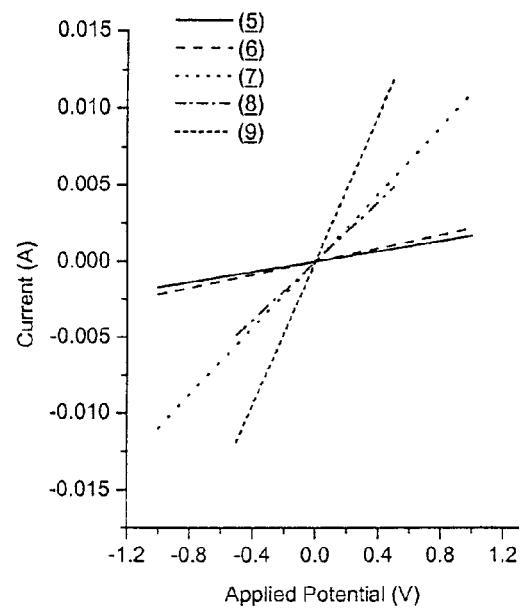

FIG. 5: I–V characteristics of Au-nanoparticles interconnected by the linker molecules 5 (-), 6 (- - -), 7 (....), 8 (.-.-.), and 9 (- - -) and self-assembled onto interdigiated Au electrode structures by the layer-by-layer assembly technique to a film thickness of approx. 30 nm.

Figure 6:
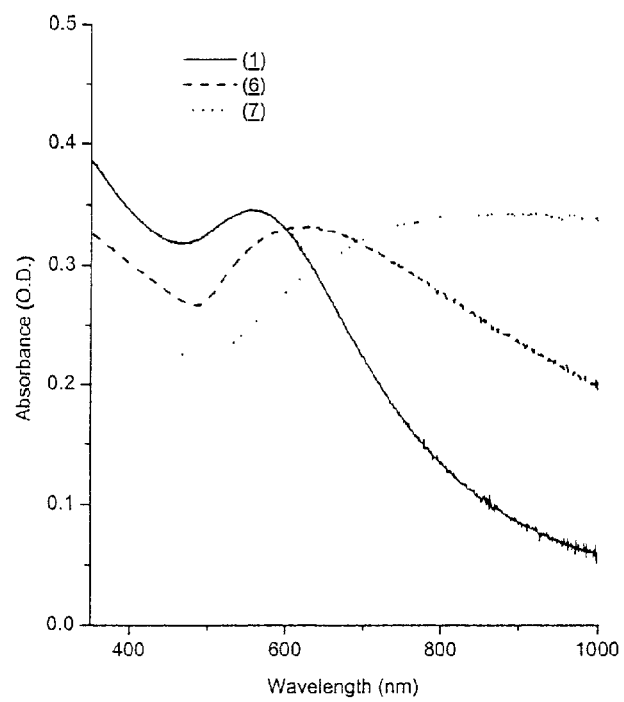

FIG. 6: Absorption spectra of Au-nanoparticles interconnected by linker molecules 1 (-), 6 (- - -), and 7 (....) assembled onto a silanized glass substrate by the layer-by-layer assembly technique to a film thickness of approx. 30 mn.

All experimental examples provided in the following section were achieved by assembling dodecylamine stabilised Au-nanoparticles interconnected by various linker molecules by the layer-by-layer assembly technique onto interdigitated electrode structures. The nanoparticles were synthesised according to a method described by Brust et al. (Leff, D. V., Brandt, L., Heath, J. R. (1996) Langmuir, 12, 4723–4730 "Synthesis and characterization of hydrophobic, organically-soluble gold nanocrystals functionalised with primary amines."), using dodecylamine as a capping molecule. Prior to the assembly process, the electrodes were functionalised with a (3-aminopropyl)-dimethylethoxysilane. For the assembly process, a 1 mM solution of the linker molecule was used and the concentration of the Au-nanoparticle solution was approx. 0.5 mM. The assembly process was monitored using UV/VIS absorption spectroscopy. The film thickness for all assemblies was adjusted to an optical density (O.D.) of approximately 0.32–0.35 at the maximum of the plasmon band, which amounts to a film thickness of roughly 30 nm as determined by AFM. The thickness of the films varies slightly from assembly to assembly. It has been verified, that these observed alterations in the film thickness introduce only a small uncertainty of ~5% in the I–V characteristics. With all assemblies, temperature dependent measurements of the conductivity were performed between ~100 K and ~300 K. The resistivity p of the assemblies were calculated according to $p=R \cdot A \cdot L^{-1}$, with A being the cross sectional area (A=30 nm 200 mm) and L=60 µm It has to be pointed out that the results obtained from these assemblies are for the following reasons average values for the multifunctional linker molecules:

The sizes of the Au-nanoparticles vary between approx. 3 and 30 nm.

The assembly of the nanoparticles was performed by the layer-by-layer assembly technique and as a result of the flexibility of the linker molecules the particle-particle distance can vary and the assembled films might contain some inhomogenities.

1) Altering the electron density in aromatic π-systems through different substitutes as it can be described through the Hammett correlation parameter $\sigma_p^+$.

Phenylene diamines exhibiting different substitutes on the 2 and 5 positions of the conjugated π-system have been used to synthesise dithiol linker molecules (dimercaptoacetamido-benzene R=H (1), R=CH$_3$ (2), and R=Cl (3), depicted in FIG. 2. The change in the electron density on the ring structure itself can be described using the so-called Hammett parameter ($\sigma_p^+$). The Hammett equation for the calculation of substituent effects on reaction rates and chemical equilibria was introduced by Hammett using the ionisation of meta and para-substituted benzoic acids. From this equation the substituent constant $\sigma_p^+$ can be obtained which are negative for electron donating substitutes and positive for electron accepting groups. These linker molecules were synthesised according to the route described in FIG. 1a. The I–V characteristics of the thin film assemblies using the three different dimercapto-acetamido benzene derivatives provide evidence, that the substitutes in positions 2 and 5 provides a means for fine tuning the conductivity through such assemblies (FIG. 3). The resistances obtained for these assemblies are summarised in Table 1. Temperature dependent measurements of the conductivity provide evidence for a thermal activated transport process FIG. 4.) The activation energy was obtained from fitting the plots $\sigma(T^{-1})$ to $$\sigma = \sigma_0 \cdot \exp\left(\frac{E_A}{k_B \cdot T}\right)$$

The activation energies obtained for these molecules are also summarised in Table 1.

TABLE 1

Summary of the resistivity ρ and the activation energy $E_A$ for the linker molecules 1–10 from FIG. 2.

| Linker molecule | ρ (Ωcm) | $E_A$ (meV) |
|---|---|---|
| 1 | 18 · 10$^1$ | 74 |
| 2 | 10 · 10$^1$ | 110 |
| 3 | 3 · 10$^2$ | 96 |
| 4 | 6.9 · 10$^2$ | 88 |
| 5 | 6.41 | 31 |
| 6 | 6.0 | 112 |
| 7 | 9.1 · 10$^{-1}$ | — |
| 8 | 10.2 · 10$^{-1}$ | 25 |
| 9 | 4.2 · 10$^{-1}$ | 15 |
| 10 | 8.7 · 10$^2$ | 42 |

2) Altering the degree of charge transport through linker molecules exhibiting conjugated π-systems;
   a) Altering the particle-particle interaction by changing the degree of conjugation in the linker molecule through cross-conjugation and/or by introducing non-conjugated molecular structures into the linker molecule.
   b) Introducing electron-accepting groups onto conjugated π-systems of the linker molecule, facilitating the electron transport across the linker molecule.

Using the same synthetic route that has been used for substituting the benzenoid derivatives FIG. 2), diaminocyclohexane has been used to synthesise a dimercaptoacetamido-cyclohexane (4) linker molecule. This system thus provides us with the possibility to directly obtain information to which degree the conductivity in these assemblies is reduced, when a conjugated system is exchanged with a non-conjugated system. The I–V characteristic of this linker molecule is also depicted in FIG. 3. The resistivity of the assembly obtained for this linker molecule is ρ=69 10$^2$ Ω cm. This provides evidence that changing the degree of conjugation of the linker molecule influences the conductivity through these assemblies.

The effect of introducing an electron acceptor as a linker molecule is demonstrated using 1, 4-dimercaptoacetamido-anthraquinone (5) and 1,8-dimercaptoacetamido-anthraquinone (6). Both linker molecules were synthesised according to the route described in FIG. 1a. The room temperature resitivity of these assemblies was found to be 2 orders of magnitude smaller than the resistances obtained from the substituted phenylene diamine rings. For both compounds, the resistance was of the same order of magnitude, ρ=6.41 Ω cm (4) and p=6.00 Ω cm (5), respectively. The I–V characteristics at room temperature are shown in FIG. 5. These measurements show that introducing electron-accepting properties of linker molecules has a pronounced effect on the conductivity through the assembly. A pronounced difference between the assemblies of Au nanoparticles interconnected with the anthraquinone derivative and the benzene derivatives is also evident in the absorption spectra of these molecules. In case of the linker molecules (1–4) the maximum of the plasmon absorption band peaked at~550 nm, while in case of the anthraquinone linker molecules the maximum was red shifted to ~620 nm (FIG. 6). Since the dielectric vicinity of the particles is similar for all of the above-described assemblies this red shift could be an indication for a strong interaction between the nanoparticles induced by the linker molecule. These results show, that cross conjugation as described by Hush et al. (Hush, N. S., Reimers, J. R., Hall, L. E., Johnston, L. A., Crossley, M. J. (1998) Annals of the New York Academy of Sciences, 852, 1–21 (Edts. Aviram, A., Ratner, M.) "Optimization and chemical control of porphyrin-based molecular wires and switches.") may not necessarily cause an attenuation of the coupling between the particles (vide supra). Hence considering the effect of cross-conjugation for tuning the conductivity in assemblies, the electron accepting properties have to be taken into consideration.

3) Influencing the charge transport properties through the contacting molecular groups CON$_{,1,2}$.

The molecular groups establishing the connection between the different nanostructured units, e.g. nanowires, nanoparticles, and possibly electrodes has a central function in the charge transport since the molecular design of this group is defining the type of bond that is formed between interconnected units. Included is also that the electrode or wire metal can be altered to alter the bonding group from the electrode/wire that participates in establishing the contact to the linker molecule depending on what type of tunnel barrier should be established for a specific interconnect.

Figure 1B:
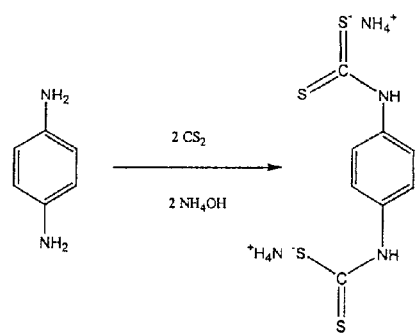

Two dithiocarbamate derivatives, dithiocarbamatobenzene (7) and dithiocarbamatocyclohexane (8) respectively, were synthesised according to the route described in FIG. 1b. Both dithiocarbamates have the same central body X as the dithiols (1) and (4) FIG. 2. The absorption characteristics of Au nanoparticles interconnected with dithiocarbamatobenzene (7) shows the typical characteristics of bulk gold (Kreibig, U., Genzel, L. (1985) Surface Science, 156, 678–700 "Optical absorption of small metallic particles."). Such absorption characteristics have been also observed using 2-mercaptoethanol for assembling Au particles into films exhibiting a thickness of~150 nm (Aguila, A. Murray, R. W. (2000), Langmuir, 16, 5949–5954 "Monolayer-protected clusters with fluorescent dansyl ligands."). In contrast, the assembly using the dithiocarbamatocyclohexane ( 8) exhibits absorption characteristics similar to the ones observed for the anthraquinone-substituted linker molecules. The plasmon band peaks at app. 620 nm and there is an increase in absorption in the near infrared. Temperature dependent studies of the dithiocarbamate assembly show typical metal behavior, i.e. with decreasing temperature an increase in the conductivity could be observed (FIG. 4). The I–V characteristics at room temperatures are shown in FIG. 5. The resistivities obtained for substances 7 and 8 are 9.1 $10^{-1}$ Ω cm and 10.2 $10-10^{-1}$ Ω cm, respectively. The corresponding value for bulk gold at 20° C. is $\rho=2.4\ 10^{-4}$ Ω cm (Weast, R. G. (Edt.) (1988) CRC Handbook of chemistry and physics, $69^{th}$ ed., CRC Press Inc. New York.). Similar resistivities have also been achieved by using a very short linker molecule, 2-mercaptoethanol and by increasing the film thickness (Aguila, A. Murray, R. W. (2000), Langmuir, 16, 5949–5954 "Monolayer-protected clusters with fluorescent dansyl ligands."). These measurements provide evidence that the binding of linker molecules to the particle has a significant effect on the room temperature resistance of these assemblies, as it has been suggested by the theoretical calculations of Emberly and Kirczenow (Emberly, E. G., Kirczenow, G. (1998) Annals of the New York Academy of Sciences, 852, 1–21 (Edts. Aviram, A., Ratner, M.) "Theory of electrical conductance through a molecule.").

4) Influencing the charge transport by altering the molecular groups at the nanoparticle/linker molecule interface:

a) Increasing the electron coupling through two interconnected circuit elements by introducing a hydrogen-bonding network into the linker molecules.

Dimercaptoacetamidooctane (9) (FIG. 2) was also used for interconnecting Au-nanoparticles into thin films. This molecule was synthesised for comparison of the I–V characteristics obtained from the commercially available nonanedithiol (10), which has been studied in detailed in the literature. Both linker molecules are quite flexible and it can be imagined that the distances between the particles may vary quite a bit. In the case of the amide substituted linker molecules (9) and (10) the resistivity ρ of the assembly are $\rho=4.2.\ 10^{-1}$ Ω cm and $\rho=8.7\ \cdot 10^{2}$ Ω cm, respectively. Although both linker molecules are of comparable length, the resistivities vary by three orders of magnitude. However, since both of the linker molecules are quite flexible, it is difficult to judge to which extent maybe a hydrogen-bond network between the amide groups could influence the charge transport.

What is claimed is:

1. A multifunctional linker molecule which is selected from the group consisting of 1,4-dimercaptoaceamidobenzene of the formula:

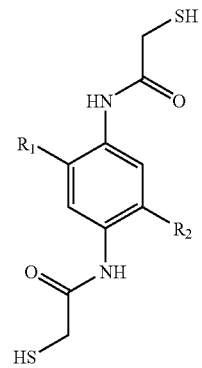

wherein $R_1$ and $R_2$ are independently selected from $CH_3$ and/or Cl, 1,4-dimercaptoacetamidocyclohexane, 1,4-dimercaptoacetamido-9, 10-anthraquinone, 1,5-dimercaptoacetamido-9,10-anthraquinone, 1,8-dimercaptoacetamidooctane, or 1,4-dithiocarbamatocyclohexane.

* * * * *